United States Patent [19]
Levine et al.

[11] 4,057,547
[45] Nov. 8, 1977

[54] AZABICYCLIC COMPOUNDS, AND PRODUCTION THEREOF

[75] Inventors: Seymour Levine, North Brunswick; Vinayak V. Kane, Princeton, both of N.J.

[73] Assignee: Ortho Pharmaceutical Corporation, Raritan, N.J.

[21] Appl. No.: 654,311

[22] Filed: Feb. 2, 1976

[51] Int. Cl.² .................. C07D 487/04; C07D 253/08

[52] U.S. Cl. .................................... 544/184; 424/249
[58] Field of Search ................................ 260/248 AS

*Primary Examiner*—John M. Ford
*Attorney, Agent, or Firm*—Benjamin F. Lambert

[57] ABSTRACT

Novel azabicyclic compounds useful for their central nervous system depressant and cardiovascular activity, methods for preparing same, and intermediates.

28 Claims, No Drawings

AZABICYCLIC COMPOUNDS, AND PRODUCTION THEREOF

BACKGROUND OF THE INVENTION

The present invention relates to novel azabicyclic compounds, methods for preparing same, and intermediates, and particularly to compounds having the following formula:

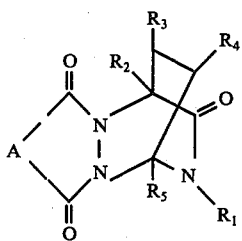

wherein: A is a member selected from the group consisting of

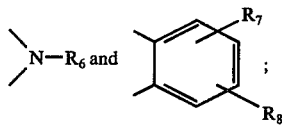

$R_1$ is a member selected from the group consisting of loweralkyl, phenyl, substituted phenyl, phenyl lower alkyl, substituted phenyl lower alkyl, loweralkylamido phenyl, and heterocyclic aryl;

$R_2$–$R_5$ are each members selected from the group consisting of hydrogen, halo, cyano, COOR', CONR'R", CH$_2$NR'R", OR''', loweralkyl, phenyl, substituted phenyl, phenyl loweralkyl, and substituted phenyl loweralkyl, said R' and R" each being a member selected from the group consisting of hydrogen and loweralkyl and said R''' being a member selected from the group consisting of hydrogen, loweralkyl, phenyl, and substituted phenyl;

$R_6$ is a member selected from the group consisting of loweralkyl, phenyl, and substituted phenyl; and $R_7$ and $R_8$ are each members selected from the group consisting of hydrogen, halo, loweralkyl, loweralkoxy, and amino.

As used herein, the terms "loweralkyl" and "loweralkoxy" mean straight or branched chain aliphatic hydrocarbons of from 1 to about 6 carbon atoms such as, for example, methyl, ethyl, isopropyl, pentyl, and the like loweralkyls, and, respectively, methoxy, ethoxy, isopropoxy, pentoxy, and the like loweralkoxys. The term "halo" includes fluoro, bromo, chloro, and iodo. The term "substituted phenyl" means phenyl substituted with from 1 to 3 members each selected from the group consisting of loweralkyl, loweralkoxy, halo, and amino.

Heterocyclic aryl groups comprise five- to ten-membered heteroaromatics wherein the hetero atoms are one or more sulfur, nitrogen, or oxygen atoms. Included are monocyclic heteroaryls comprising five to six members having at least one sulfur, nitrogen or oxygen atom as the heteroatom, and bicyclic heteroaryls having up to ten members and having, as one of the cyclic moieties, a five to six membered heteroaromatic ring with at least one sulfur, nitrogen or oxygen atom as the heteroatom. Specific examples of such groups are pyridyl, quinolyl, imidazolyl, pyrazinyl, pyrrolyl, thienyl, thiazolyl, thiadiazolyl, pyrazolyl, triazolyl, oxazolyl and pyrimidinyl. The azaheterocyclic aryls may, if so desired, be further substituted at the ring carbon and nitrogen atoms. For example, the heterocyclic moiety may be substituted with a lower alkyl, e.g., 6-methyl-2-pyridyl, 4-ethyl-2-pyrimidyl, and the like; or, for example, a 2-pyrrolyl moiety may be alkylated to the corresponding N-alkyl-2-pyrrolyl. Further, the carbon heterocyclic aryl linkage may be at any one of the several carbon atoms of the heterocycle as, for example, at the 2-,3-, or 4-position of the pyridyl moiety.

The compounds of formula (I) wherein A is

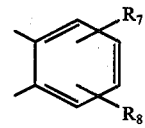

may be prepared by reacting a pyridone of formula (II) with a suitable phthalazinedione of formula (III) in a suitable inert organic solvent, as for example, acetone, acetonitrile, dichloromethane, chloroform, or the like. The solvent must be inert to the reactants and must remain a liquid at the temperature of the reaction. The reaction may be conducted at temperatures up to ambient, but cooling is preferred. Best results have been obtained at about −60° C. The pyridone is preferably employed in excess. The reaction is usually completed after about 2 hours, at which time the intermediate of formula (IV) may be isolated by conventional techniques or may be used without isolation. This intermediate is then reduced by conventional hydrogenation techniques to yield the desired product of formula (I). This reaction may be conducted in a lower alkanol, such as methanol, ethanol, and the like; ethyl acetate; methylene chloride; mixtures thereof; and the like as solvent. A preferred solvent is a mixture of dichloromethane and methanol. Any hydrogenation catalyst may be used, such as a platinium or palladium catalyst, e.g. Pd/C, Pd/BaSO$_4$, Pd/CaCO$_3$, or the like. Hydrogen pressure may be atmospheric or greater. Removal of the catalyst by filtration or the like, concentration of the filtrate, and isolation and purification of the resulting product of conventional means yields the compound of formula (I). This reaction scheme may be illustrated by the following, wherein $R_1$–$R_8$ are as previously defined, $R'_1$ is a member selected from the group consisting of loweralkyl, phenyl, substituted phenyl, phenyl loweralkyl, substituted phenyl loweralkyl, nitrophenyl, and heterocyclic aryl, and $R_7'$ and $R_8'$ are each members selected from the group consisting of hydrogen, halo, loweralkyl, loweralkoxy, amino, and nitro:

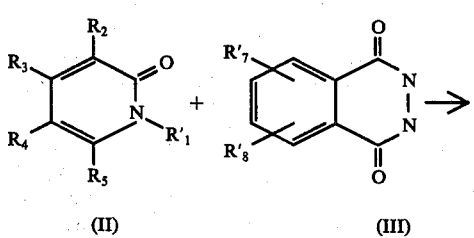

-continued

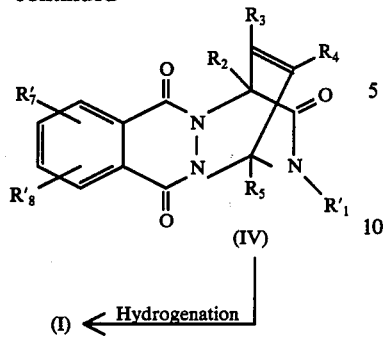

(I) ← Hydrogenation (IV)

The compounds of formula (I) where A is

may be prepared by the same procedure, substituting a suitable 4-substituted urazole of formula (V) for the phthalazinedione of formula (III) used above. The same solvent and temperature conditions may be employed in this reaction as in the above-described reaction, but preferably equivalent amounts of the two reactants are employed. Best results have been obtained at about 0° C. This reaction scheme may be illustrated by the following, wherein $R_1$-$R_6$ and $R'_1$ are as previously defined:

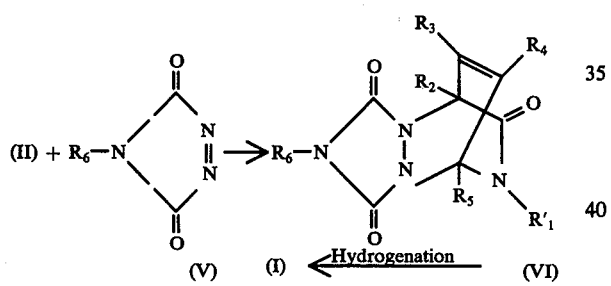

Compounds of formula (I) wherein $R_1$ is azaheterocyclic aryl may be converted to the corresponding pharmaceutically acceptable quaternary salts by reaction with a suitable quaternizing agent, e.g., lower alkyl iodides such as methyl iodide and the like. These quaternary salts are considered part of the present invention.

The starting materials of formulas (III) and (V) are known or may be prepared by known techniques described in, for example, *J. Amer. Chem. Soc.*, 84,966(1962); J. Thiele and O. Stange, *Ann.*, 283, 1(1849); G. Zinner and W. Denker, *Arch. Pharm.*, 294, 370(1961); and J. C. Stickler and W. H. Pirkle, *J. Org. Chem.*, 31, 3445(1961). The pyridones of formula (II) are generally known. See, for example, "The Chemistry of Heterocyclic Compounds-Pyridine and its Derivatives," Volume 14 Supplement part 3, R. Abramovich, Editor, pages 597–1180, J. Wiley & Sons.

Compounds of formula (I) have central nervous system modifying activity, particularly as depressants, and are therefore useful as tranquilizers. The preferred dosage level is from about 30 mg/kg to about 300 mg/kg. In addition, they have cardiovascular activity and are thus useful in the treatment of bradycardia and as cardiotonic agents. For use as cardiovascular agents, the compounds are preferably administered at dosage levels ranging from about 50 mg/kg to about 100 mg/kg.

The compounds of formulas (IV) and (VI) are novel and are useful as intermediates in the preparation of compounds of formula (I). These novel intermediates are also considered to be part of the present invention and may be represented by the following general formula:

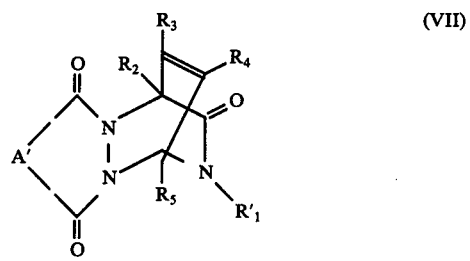

(VII)

wherein A' is a member selected from the group consisting of

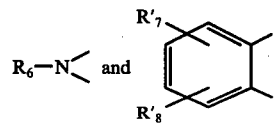

The methods described whereby the compounds of formula (I) are prepared are novel and are thus also considered to be part of the present invention.

The preferred compounds of formula (I) of the invention are those wherein $R_2$-$R_5$ are hydrogen, $R_6$ is a member selected from the group consisting of phenyl and substituted phenyl, and $R_7$ and $R_8$ are hydrogen. The more preferred compounds of the invention are those wherein A is

$R_2$-$R_5$ are hydrogen, and $R_6$ is phenyl. The most preferred compounds of the invention are those wherein A is

$R_2$, $R_3$ and $R_5$ are hydrogen; $R_4$ is a member selected from the group consisting of hydrogen and loweralkyl, $R_6$ is phenyl, and $R_1$ is a member selected from the group consisting of phenyl, substituted phenyl, and phenyl alkyl.

The present invention is illustrated by the following examples:

EXAMPLE I 1,2-Dihydro-2-methyl-13,14-ethanol[1,2,4]-triazino[2,1-b]-phthalazine-3,6,11(4H)-trione To a solution of t-butyl hypochlorite (3.8 g, 0.038 m) in acetone (200 ml) which was cooled to −60°, was added the sodium salt of phthalhydrazide (4.8 g, 0.021 m). After 2.5 hours at −60° to −50°, the green reaction mixture was filtered to give a clear green solution of 1,4-phthalazinedione. 1-Methyl-2-pyridone (2.0 g, 1.8 eq., based on reacted phthalhyrazide) was added to the green solution and the resulting solution was kept at −60° for 40 minutes, allowed to warm up to 0°, and then kept at 0° for another hour. The light green solution was concentrated under reduced pressure to a volume of 10 ml. Addition of ether (30 ml) precipitated the crude product which was collected by filtration (1.8g).

This material was dissolved in a solution of $CH_2Cl_2$ and MeOH (1:1, 60 ml). After the addition of 10% Pd/C (0.4g), the resulting suspension was hydrogenated for one hour under 30 psi. The catalyst was removed by filtration and the colorless filtrate was concentrated under reduced pressure until crystallization took place. Filtration and recrystallization from $CH_2Cl_2$/ether afforded white granules of 1,2-dihydro-2-methyl-13,14-ethanol[1,2,4]-triazino[2,1-b]phthalazine-3,6,11(4H)-trione.

Anal. Calcd for $C_{14}H_{13}N_3O_3$: C, 61.98; H, 4.83; N, 15.49; Found: C, 61.99; H, 4.87; N, 15.50.

EXAMPLE II 5,6-Dihydro-6-(4-fluorophenyl)-2-phenyl-2H-5,8-ethano-[1,2,4]triazolo[1,2-a]-[1,2,4]-triazine-1,3,7(8H)-trione $N_2O_4$ was bubbled into a cooled (5°) suspension of phenyl urazole (5.0g, 0.333 m) and $Na_2SO_4$ (8.0 g) in $CH_2Cl_2$ (200 ml). After 5 minutes, the $Na_2SO_4$ was removed by filtration and the resulting deep-red colored filtrate was concentrated to dryness under reduced pressure at 20°. To the 4-phenyl-1,2,4-triazoline-3,5-dione (4.0g) dissolved in acetone (60 ml) was added 1-methyl-2-pyridone (6.2 g, 0.066 m). The deep-red colored solution was kept at room temperature for 30 minutes, and was then cooled to 0°. After 1 hour at 0°, the precipitate was collected by filtration and washed with cold MeOH. The precipitate (3.0g) was immediately dissolved in a solution of $CH_2Cl_2$ and MeOH (1:1, 80 ml). After the addition of 5% Pd/C (1.0g), the resulting suspension was hydrogenated for 1 hour under 30 psi. The catalyst was removed by filtration and the filtrate was concentrated to give a yellow oil. The yellow oil was triturated with MeOH, chilled, and filtered to give the crude product, which was recrystallized from EtOAc/hexane to yield white microprisms of 5,6-dihydro-6-(4-fluorophenyl)-2-phenyl-2H-5,8-ethano-[1,2,4]triazolo[1,2-a]-[1,2,4]-triazine-1,3,7(8H)-trione; m.p. 167°-168° C.

Anal. Calcd. for $C_{14}H_{14}N_4O_3$: C, 58.73; H, 4.93; N, 19.57; Found: C, 58.89; H, 5.11; N, 19.67.

EXAMPLE III

Following the procedure of Example I, but substituting equivalent amounts of the appropriate pyridone for the 1-methyl-2-pyridone used therein, there are obtained the following:

1,2-dihydro-2-(2-phenylethyl)-13,14-ethanol[1,2,4]-triazino[2,1-b]phthalazine-3,6,11(4H)-trione; m.p. 223°-225° C; and 1,2-dihydro-2-phenylmethyl-13,14-ethanol[1,2,4]-triazino[2,1-b]phthalazine-3,6,11(4H)-trione; m.p. 154°-157° C.

EXAMPLE IV

Following the procedure of Example II, but substituting equivalent amounts of the appropriate pyridone for the 1-methyl-2-pyridone used therein, there are obtained the following:

5,6-dihydro-2,6-diphenyl 2H-5,8-ethano[1,2,4]-triazolo[1,2-a][1,2,4]-triazine-1,3,7 (8H)-trione; m.p. 214°-215° C;

5,6-dihydro-2,6-diphenyl-11-methyl-2H-5,8-ethano-[1,2,4]triazolo[1,2-a][1,2,4]-triazine-1,3,7(8H)-trione; m.p. 157°-158° C;

5,6-dihydro-2-phenyl-6-(phenylmethyl)-2H-5,8-ethano[1,2,4]triazolo[1,2,-a]-triazine-1,3,7(8H)-trione; m.p. 194°-195° C;

5,6-dihydro-2-phenyl-6-(2-phenylethyl)-2H-5,8-ethanol[1,2,4]triazolo[1,2-a][1,2,4]-triazine-1,3,7(8H)-trione; m.p. 155°-156° C;

5,6-dihydro-6-(4-fluorophenyl)-2H-5,8-ethano-[1,2,4]triazolo[1,2-a][1,2,4]-triazine-1,3,7(8H)-trione; m.p. 225°-226° C;

5,6-dihydro-6-(4-methoxyphenyl)-2-phenyl-2H-5,8-ethano[1,2,4]-triazolo[1,2-a][1,2,4]-triazine-1,3,7-(8H)-trione; m.p. 164°-166° C;

5,6-dihydro-2-phenyl-6-(2-thienyl)-2H-5,8-ethano-[1,2,4]triazolo[1,2-a][1,2,4]-triazine-1,3,7(8H)-trione; m.p. 190°-191° C; and 5,6-dihydro-2-phenyl-6-(3-pyridyl)-2H-5,8-ethano-[1,2,4]-triazolo[1,2-a][1,2,4]-triazine-1,3,7(8H)-trione methiodide; m.p. 238°-244° C.

This last compound was converted to the methyl quaternary salt by treatment with methyl iodide in acetonitrile.

EXAMPLE V

Following the procedure of Example II, but substituting N-(4'-nitrophenyl)-2-pyridone for the 1-methyl-2-pyridone used therein, there is prepared the corresponding 4-nitrophenyl intermediate. Hydrogenation of this intermediate according to the procedure of Example II, yields the corresponding 4-aminophenyl product which upon treatment with acetic anhydride yields 6-(4-acetamidophenyl)-5,6-dihydro-2-phenyl-2H-5,8-ethano-[1,2,4]-triazolo-[1,2-a][1,2,4]-triazine-1,3,7(8H)-trione; m.p. 144°-145° C.

EXAMPLE VI

Following the procedure of Example I, but substituting equivalent amounts of the appropriate pyridone and phthalazinedione for the 1-methyl-2-pyridone and 1,4-phthalazinedione used therein, the following intermediates are obtained:

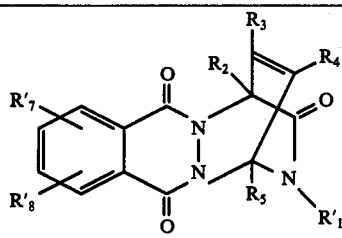

| R'₁ | R₂ | R₃ | R₄ | R₅ | R'₇ | R'₈ |
|---|---|---|---|---|---|---|
| ethyl | 4-chlorophenyl | H | H | H | H | H |
| phenyl | H | —Cl | H | H | 8-Cl | H |
| phenyl | —CH₃ | H | —COOH | H | H | H |
| phenyl | H | H | —COOCH₃ | H | 8-Cl | 9-Cl |
| phenyl | H | H | —CONHCH₃ | H | H | H |
| 4-chlorophenyl | H | —OCH₃ | H | H | H | H |
| 2-thienyl | H | H | H | benzyl | H | H |
| 3-pyridyl | H | phenyl | H | H | H | H |
| phenethyl | H | —CN | H | H | H | H |
| benzyl | H | —OCH₃ | H | —CH₃ | H | H |
| ethyl | H | H | —OH | H | H | H |
| benzyl | H | —OC₆H₅ | H | H | H | H |
| phenethyl | —OCH₃ | H | 4-fluorophenoxy | H | H | H |
| benzyl | H | H | H | 4-chlorophenyl | 9-NO₂ | H |
| benzyl | —Cl | H | H | H | 8-NH₂ | H |
| benzyl | H | H | H | H | 7-Br | 9-Br |
| benzyl | H | H | H | H | 8-CH₃ | H |
| benzyl | H | H | H | H | 9-CH₂OCH₃ | H |
| 4-chlorobenzyl | —Cl | H | H | —Cl | H | H |
| 3,4-dimethoxyphenyl | —COOH | H | H | —COOH | H | H |
| benzyl | phenyl | H | H | H | 8-OCH₃ | H |

EXAMPLE VII

Following the reduction procedure of Example I, but substituting an equivalent amount of an intermediate prepared in Example III for the intermediate used therein, the following products are obtained:

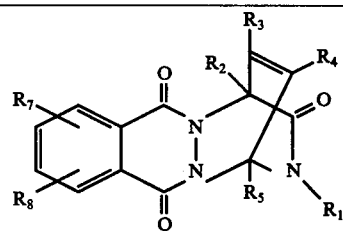

| R₁ | R₂ | R₃ | R₄ | R₅ | R₇ | R₈ |
|---|---|---|---|---|---|---|
| ethyl | 4-chlorophenyl | H | H | H | H | H |
| phenyl | H | —Cl | H | H | 3-Cl | H |
| phenyl | —CH₃ | H | —COOH | H | H | H |
| phenyl | H | H | —COOCH₃ | H | 8-Cl | 9-Cl |
| phenyl | H | H | —CONHCH₃ | H | H | H |
| 4-chlorophenyl | H | —OCH₃ | H | H | H | H |
| 2-thienyl | H | H | H | benzyl | H | H |
| 3-pyridyl | H | phenyl | H | H | H | H |
| phenethyl | H | —CN | H | H | H | H |
| benzyl | H | —OCH₃ | H | —CH₃ | H | H |
| ethyl | H | H | —OH | H | H | H |
| benzyl | H | —OC₆H₅ | H | H | H | H |
| phenethyl | —OCH₃ | H | 4-fluorophenoxy | H | H | H |
| benzyl | H | H | H | 4-chlorophenyl | 9-NH₂ | H |
| benzyl | —Cl | H | H | H | 8-NH₂ | H |
| benzyl | H | H | H | H | 7-Br | 9-Br |
| benzyl | H | H | H | H | 8-CH₃ | H |
| benzyl | H | H | H | H | 9-CH₂OCH₃ | H |
| 4-chlorobenzyl | —Cl | H | H | —Cl | H | H |
| 3,4-dimethoxy phenyl | —COOH | H | H | —COOH | H | H |

-continued

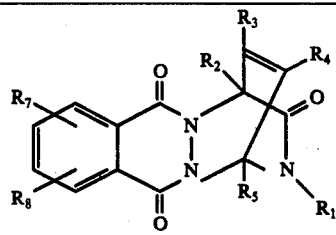

| R₁ | R₂ | R₃ | R₄ | R₅ | R₇ | R₈ |
|---|---|---|---|---|---|---|
| benzyl | phenyl | H | H | H | 8-OCH₃ | H |

EXAMPLE VIII

Following the procedure of Example II, but substituting equivalent amounts of the appropriate pyridone and urazole for the 1-methyl-2-pyridone and phenyl urazole used therein, the following intermediates are obtained:

EXAMPLE IX

Following the reduction procedure of Example II, but substituting an equivalent amount of an intermediate prepared in Example VII for the intermediate used therein, the following products are prepared:

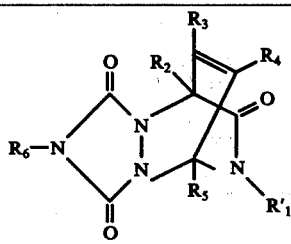

| R'₁ | R₂ | R₃ | R₄ | R₅ | R₆ |
|---|---|---|---|---|---|
| isopropyl | 4-chlorophenyl | H | H | H | 4-chlorophenyl |
| phenyl | —Cl | —Cl | H | H | ethyl |
| ethyl | —CH₃ | H | H | —Cl | phenyl |
| phenyl | H | —CN | H | —CH₃ | phenyl |
| benzyl | H | —COOH | —COOH | H | phenyl |
| phenyl | H | H | —COOCH₃ | H | phenyl |
| phenethyl | H | H | —CONH₃ | phenyl | phenyl |
| phenyl | H | —CH₂N(CH₃)₂ | H | H | phenyl |
| benzyl | H | H | 4-chlorophenyl | H | phenyl |
| phenyl | H | benzyl | H | —CH₃ | methyl |
| phenyl | H | —OCH₃ | H | H | phenyl |
| 4-fluorophenyl | H | —OC₆H₅ | H | H | phenyl |
| 2-thienyl | H | H | —OH | H | phenyl |
| phenethyl | H | 4-chlorophenoxy | H | H | phenyl |
| benzyl | —COOH | H | —Cl | H | 3,4-dimethoxyphenyl |
| benzyl | —CN | —CN | H | H | phenyl |
| benzyl | H | H | H | —CH₂N(C₂H₅)₂ | methyl |
| phenyl | H | H | —OC₆H₅ | H | phenyl |
| phenyl | phenyl | phenyl | H | H | ethyl |
| phenyl | benzyl | H | H | benzyl | phenyl |

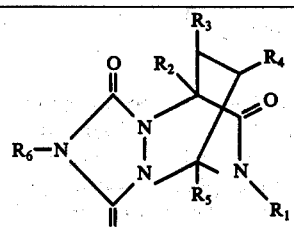

| R₁ | R₂ | R₃ | R₄ | R₅ | R₆ |
|---|---|---|---|---|---|
| isopropyl | 4-chlorophenyl | H | H | H | 4-chlorophenyl |
| phenyl | —Cl | —Cl | H | H | ethyl |
| ethyl | —CH₃ | H | H | —Cl | phenyl |
| phenyl | H | —CN | H | —CH₃ | phenyl |

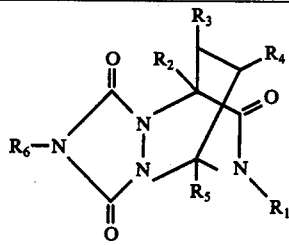

| R₁ | R₂ | R₃ | R₄ | R₅ | R₆ |
|---|---|---|---|---|---|
| benzyl | H | —COOH | —COOH | H | phenyl |
| phenyl | H | H | —COOCH₃ | H | phenyl |
| phenyl-ethyl | H | H | —CONH₂ | phenyl | phenyl |
| phenyl | H | —CH₂N(CH₃)₂ | H | H | phenyl |
| benzyl | H | H | 4-chloro-phenyl | H | phenyl |
| phenyl | H | benzyl | H | —CH₃ | methyl |
| phenyl | H | —OCH₃ | H | H | phenyl |
| 4-fluoro-phenyl | H | —OC₆H₅ | H | H | phenyl |
| 2-thienyl | H | H | —OH | H | phenyl |
| phen-ethyl | H | 4-chloro-phenoxy | H | H | phenyl 3,4-dimeth-oxyphenyl |
| benzyl | —COOH | H | —Cl | H | phenyl |
| benzyl | —CN | —CN | H | H | phenyl |
| benzyl | H | H | H | CH₂N(C₂H₅)₂ | methyl |
| phenyl | H | H | —OC₆H₅ | H | phenyl |
| phenyl | phenyl | phenyl | H | H | ethyl |
| phenyl | benzyl | H | H | benzyl | phenyl |

The above examples have been provided only by way of illustration and not to limit the scope of the present invention, which scope is defined only in the appended claims.

What is claimed is:

1. A compound having the formula:

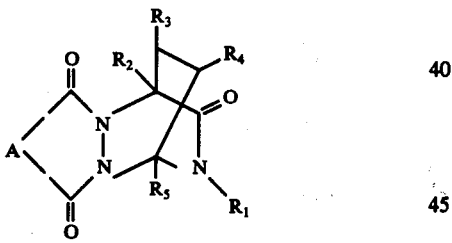

wherein:

A is a member selected from the group consisting of

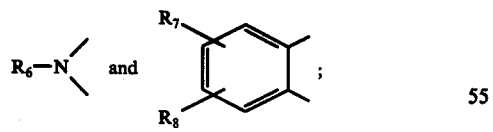

$R_1$ is a member selected from the group consisting of loweralkyl, phenyl, substituted phenyl wherein the substituent is 1–3 groups selected from loweralkyl, loweralkoxy, halo and amino, phenyl loweralkyl, substituted phenyl loweralkyl wherein the substituent is 1–3 groups selected from loweralkyl, loweralkoxy, halo and amino, loweralkylaminodophenyl, and heterocyclic aryl selected from pyridyl, quinolyl, imidazolyl, pyrazinyl, pyrrolyl, thienyl, thiazolyl, thiadiazolyl, pyrazolyl, triazolyl, oxazolyl and pyrimidinyl;

$R_2$–$R_5$ are each members selected from the group consisting of hydrogen, halo, cyano, COOR′, CONR′R″, CH₂NR′R″, OR‴, loweralkyl, phenyl, substituted phenyl wherein the substituent is 1–3 groups selected from loweralkyl, loweralkoxy, halo and amino, phenyl loweralkyl, and substituted phenyl loweralkyl wherein the substituent is 1–3 groups selected from loweralkyl, loweralkoxy, halo and amino, said R′ and R″ each being a member selected from the group consisting of hydrogen and loweralkyl and said R‴ being a member selected from the group consisting of hydrogen, loweralkyl, phenyl and substituted phenyl wherein the substituent is 1–3 groups selected from loweralkyl, loweralkoxy, halo and amino;

$R_6$ is a member selected from the group consisting of loweralkyl, phenyl, and substituted phenyl wherein the substituent is 1–3 groups selected from loweralkyl, loweralkoxy, halo and amino; and $R_7$ and $R_8$ are each members selected from the group consisting of hydrogen, halo, loweralkyl, loweralkoxy, and amino; and pharmaceutically acceptable quaternary salts thereof wherein $R_1$ is pyridyl, quinolyl, imidazolyl, pyrazinyl, pyrrolyl, thiazolyl, thiadiazolyl, pyrazolyl, triazolyl, oxazolyl or pyrimidinyl.

2. The compound of claim 1 wherein $R_2$, $R_3$, $R_4$, and $R_5$ are hydrogen; $R_6$ is a manner selected from the group consisting of phenyl wherein the substituent is 1—3 groups selected from loweralkyl, loweralkoxy, halo and amino; and $R_7$ and $R_8$ are hydrogen.

3. A compound having the formula:

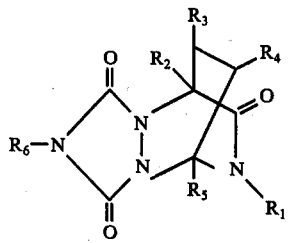

wherein:
R₁ is a member selected from the group consisting of loweralkyl, phenyl, substituted phenyl wherein the substituent is 1-3 groups selected from loweralkyl, loweralkoxy, halo and amino, phenyl loweralkyl, substituted phenyl loweralkyl wherein the substituent is 1-3 groups selected from loweralkyl, loweralkoxy, halo and amino, loweralkylamidophenyl, and heterocyclic aryl selected from pyridyl, quinolyl, imidazolyl, pyrazinyl, pyrrolyl, thienyl, thiazolyl, thiadiazolyl, pyrazolyl, triazolyl, oxazolyl and pyrimidinyl;

R₂-R₅ are each members selected from the group consisting of hydrogen, halo, cyano, COOR', CONR'R", CH₂NR'R", OR''', loweralkyl, phenyl, substituted phenyl wherein the substituent is 1-3 groups selected from loweralkyl, loweralkoxy, halo and amino, phenyl loweralkyl, and substituted phenyl loweralkyl wherein the substituent is 1-3 groups selected from loweralkyl, loweralkoxy, halo and amino, said R' and R" each being a member selected from the group consisting of hydrogen and loweralkyl and said R''' being a member selected from the group consisting of hydrogen, loweralkyl, phenyl, and substituted phenyl wherein the substituent is 1-3 groups selected from loweralkyl, loweralkoxy, halo and amino; and R₆ is a member selected from the group consisting of loweralkyl, phenyl, and substituted phenyl wherein the substituent is 1-3 groups selected from loweralkyl, loweralkoxy, halo and amino; and pharmaceutically acceptable quaternary salts thereof wherein R₁ is pyridyl, quinolyl, imidazolyl, pyrazinyl, pyrrolyl, thiazolyl, thiadiazolyl, pyrazolyl, triazolyl, oxazolyl or pyrimidinyl.

4. The compound of claim 3 wherein R₂, R₃, R₄, and R₅ are hydrogen; and R₆ is phenyl.

5. The compound of claim 3 wherein R₂, R₃, and R₅ are hydrogen, R₄ is a member selected from the group consisting of hydrogen and loweralkyl, R₆ is phenyl, and R₁ is a member selected from the group consisting of phenyl, substituted phenyl wherein the substituent is 1-3 groups selected from loweralkyl, loweralkoxy, halo and amino, and phenyl loweralkyl.

6. The compound of claim 3 which is 5,6-dihydro-6-methyl-2-phenyl-2H-5,8-ethanol[1,2,4]triazolo[1,2-a][1,2,4]triazine-1,3,7(8H)-trione.

7. The compound of claim 3 which is 5,6-dihydro-2,6-diphenyl-2H-5,8-ethano[1,2,4]triazolo[1,2-a][1,2,4]triazine-1,3,7(8H)-trione.

8. The compound of claim 3 which is 5,6-dihydro-2,6-diphenyl-11-methyl-2H-5,8-ethano[1,2,4]triazolo[1,2-a]-[1,2,4]-triazine-1,3,7(8H)-trione.

9. The compound of claim 3 which is 5,6-dihydro-2-phenyl-6-(phenylmethyl)-2H-5,8-ethano[1,2,4]-triazolo-[1,2-a][1,2,4]-triazine-1,3,7(8H)-trione.

10. The compound of claim 3 which is 5,6-dihydro-2-phenyl-6-(2-phenylethyl)-2H-5,8-ethano[1,2,4]triazolo-[1,2-a][1,2,4]-triazine-1,3,7(8H)-trione.

11. The compound of claim 3 which is 5,6-dihydro-6-(4-fluorophenyl)-2-phenyl-2H-5,8-ethano[1,2,4]-triazolo[1,2-a]-[1,2,4]-triazine-1,3,7(8H)-trione.

12. The compound of claim 3 which is 5,6-dihydro-6-(4-methoxyphenyl)-2-phenyl-2H-5,8-ethano[1,2,4]-triazolo[1,2-a]-[1,2,4]-triazine-1,3,7(8H)-trione.

13. The compound of the claim 3 which is 5,6-dihydro-2-phenyl-6-(2-thienyl)-2H-5,8-ethanol[1,2,4]-triazolo[1,2,-a]-[1,2,4]-triazine-1,3,7(8H)-trione.

14. The compound of claim 3 which is 5,6-dihydro-2-phenyl-6-(3-pyridyl)-2H-5,8-ethano[1,2,4]-triazolo [1,2-a][1,2,4]-triazine-1,3,7(8H)-trione and pharmaceutically acceptable quaternary salts thereof.

15. The compound of claim 3 which is 6-(4-acetamido)-5,6-dihydro-2-phenyl-2H-5,8-ethano[1,2,4]-triazolo-[1,2,4]-triazine-1,3,7(8H)-trione.

16. A compound having the formula:

wherein:
R₁ is a member selected from the group consisting of loweralkyl, phenyl, substituted phenyl wherein the substituent is 1-3 groups selected from loweralkyl, loweralkoxy, halo and amino, phenyl loweralkyl, substituted phenyl loweralkyl wherein the substituent is 1-3 groups selected from loweralkyl, loweralkoxy, halo and amino, loweralkylamidophenyl, and heterocyclic aryl selected from pyridyl, quinolyl, imidazolyl, pyrazinyl, pyrrolyl, thienyl, thiazolyl, thiadiazolyl, pyrazolyl, triazolyl, oxazolyl and pyrimidinyl;

R₂-R₅ are each members selected from the group consisting of hydrogen, halo, cyano, COOR', CONR'R", CH₂NR'R", OR''', loweralkyl, phenyl, substituted phenyl wherein the substituent is 1-3 groups selected from loweralkyl, loweralkoxy, halo and amino, phenyl loweralkyl, and substituted phenyl loweralkyl wherein the substituent is 1-3 groups selected from loweralkyl, loweralkoxy, halo and amino, said R' and R" each being a member selected from the group consisting of hydrogen and loweralkyl and R''' being a member selected from the group consisting of hydrogen, loweralkyl, phenyl and substituted phenyl wherein the substituent is 1-3 groups selected from loweralkyl, loweralkoxy, halo and amino; and R₇ and R₈ are each members selected from the group consisting of hydrogen, halo, loweralkyl, loweralkoxy, and amino; and pharmaceutically acceptable quaternary salts thereof wherein R₁ is pyridyl, quinolyl, imidazolyl, pyrazinyl, pyrrolyl, thiazolyl, thiadiazolyl, pyrazolyl, triazolyl, oxazolyl or pyrimidinyl.

17. The compound of claim 16 which is 1,2-dihydro-2-methyl-13,14-ethano[1,2,4]-triazino[2,1-b]phthalazine-3,6,11(4H)-trione.

18. The compound of claim 16 which is 1,2-dihydro-2-(1-phenylethyl)-13,14-ethano[1,2,4]-triazino[2,1-b]-phthalazine-3,6,11(4H)-trione.

19. The compound of claim 16 which is 1,2-dihydro-2-(phenylmethyl)-13,14-ethano[1,2,4]-triazino[2,1-b]phthalazine-3,6,11(4H)-trione.

20. A compound having the formula:

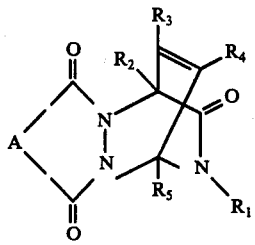

wherein:
A' is a member selected from the group consisting of

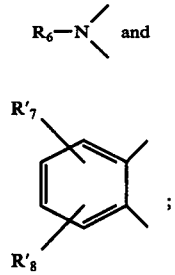

R'$_1$ is a member selected from the group consisting of loweralkyl, phenyl, substituted phenyl wherein the substituent is 1-3 groups selected from loweralkyl, loweralkoxy, halo and amino, phenyl loweralkyl, substituted phenyl loweralkyl wherein the substituent is 1-3 groups selected from loweralkyl, loweralkoxy, halo and amino, nitrophenyl, and heterocyclic aryl selected from pyridyl, quinolyl, imidazolyl, pyrazinyl, pyrrolyl, thienyl, thiazolyl, thiadiazolyl, pyrazolyl, triazolyl, oxazolyl and pyrimidinyl;

R$_2$-R$_5$ are each members selected from the group consisting of hydrogen, halo, cyano, COOR', CONR'R", CH$_2$NR'R", OR''', loweralkyl, phenyl, substituted phenyl wherein the substituent is 1-3 groups selected from loweralkyl, loweralkoxy, halo and amino, phenyl loweralkyl, and substituted phenyl loweralkyl wherein the substituent is 1-3 groups selected from loweralkyl, loweralkoxy, halo and amino, said R' and R" each being a member selected from the group consisting of hydrogen and loweralkyl and said R''' being a member selected from the group consisting of hydrogen, loweralkyl, phenyl, and substituted phenyl wherein the substituent is 1-3 groups selected from loweralkyl, loweralkoxy, halo and amino;

R$_6$ is a member selected from the group consisting of loweralkyl, phenyl and substituted phenyl wherein the substituent is 1-3 groups selected from loweralkyl, loweralkoxy, halo and amino; and R'$_7$ and R'$_8$ are each members selected from the group consisting of hydrogen, halo, loweralkyl, loweralkoxy, amino, and nitro.

21. A method of preparing a compound of claim 20 of the formula

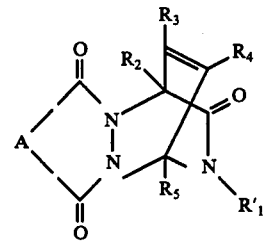

which comprises reacting together in a suitable inert organic solvent a compound of formula:

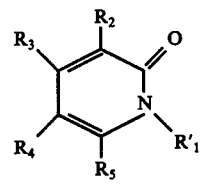

with a compound of the formula:

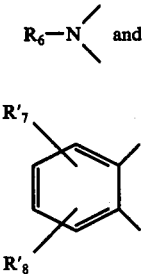

wherein:
A' is a member selected from the group consisting of

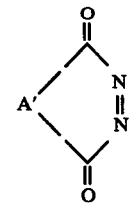

R'$_1$ is a member selected from the group consisting of loweralkyl, phenyl, substituted phenyl wherein the substituent is 1-3 groups selected from loweralkyl, loweralkoxy, halo and amino, phenyl loweralkyl, substituted phenyl loweralkyl wherein the substituent is 1-3 groups selected from loweralkyl, loweralkoxy, halo and amino, nitrophenyl, and heterocyclic aryl selected from pyridyl, quinolyl, imidazolyl, pyrazinyl, pyrrolyl, thienyl, thiazolyl, thiadiazolyl, pyrazolyl, triazolyl, oxazolyl and pyrimidinyl;

R$_2$-R$_5$ are each members selected from the group consisting of hydrogen, halo, cyano, COOR', CONR'R", CH$_2$NR'R", OR''', loweralkyl, phenyl, substituted phenyl wherein the substituent is 1-3 groups selected from loweralkyl, loweralkoxy, halo and amino, phenyl loweralkyl, and substituted phenyl loweralkyl wherein the substituent is 1-3 groups selected from loweralkyl, loweralkoxy, halo and amino, said R' and R" each being a member selected from the group consisting of hydrogen and loweralkyl and said R'" being a member selected from the group consisting of hydrogen, loweralkyl, phenyl, and substituted phenyl wherein the substituent is 1-3 groups selected from loweralkyl, loweralkoxy, halo and amino;

$R_6$ is a member selected from the group consisting of loweralkyl, phenyl, and substituted phenyl wherein the substituent is 1-3 groups selected from loweralkyl, loweralkoxy, halo and amino; and $R'_7$ and $R'_8$ are each members selected from the group consisting of hydrogen, halo, loweralkyl, loweralkoxy, amino and nitro.

22. The method of claim 21 wherein the suitable inert organic solvent is a member selected from the group consisting of acetone, acetonitrile, dichloromethane, and chloroform.

23. The method of claim 22 wherein the temperature of reaction is below ambient.

24. The method of claim 23 wherein

A' is 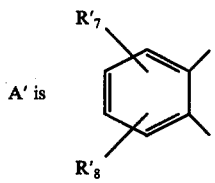

and wherein the compound

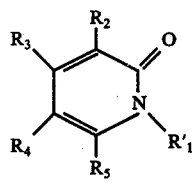

is present in excess.

25. The method of claim 24 wherein the temperature of the reaction is about $-60°$ C.

26. The method of claim 23 wherein A' is

and wherein the reactants are present in equivalent amounts.

27. The method of claim 26 wherein the temperature of the reaction is about $0°$ C.

28. A method of preparing a compound of claim 1 of the formula:

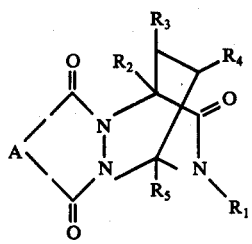

which comprises hydrogenating a compound of formula:

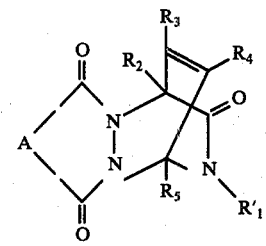

wherein:

A is a member selected from the group consisting of

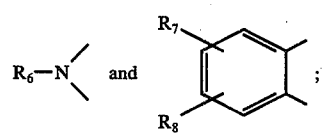

A' is a member selected from the group consisting of

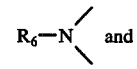

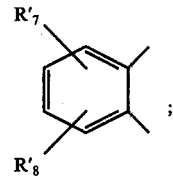

$R'_1$ is a member selected from the group consisting of loweralkyl, phenyl, substituted phenyl wherein the substituent is 1-3 groups selected from loweralkyl, loweralkoxy, halo and amino, phenyl loweralkyl, substituted phenyl loweralkyl wherein the substituent is 1-3 groups selected from loweralkyl, loweralkoxy, halo and amino, nitrophenyl, and heterocyclic aryl selected from pyridyl, quinolyl, imidazolyl, pyrazinyl, pyrrolyl, thienyl, thiazolyl, thiadiazolyl, pyrazolyl, triazolyl, oxazolyl and pyrimidinyl;

$R_1$ is a member selected from the group consisting of loweralkyl, phenyl, substituted phenyl wherein the substituent is 1-3 groups selected from loweralkyl, loweralkoxy, halo and amino, phenyl loweralkyl, substituted phenyl loweralkyl wherein the substituent is 1-3 groups selected from loweralkyl, loweralkoxy, halo and amino, loweralkylamidophenyl, and heterocyclic aryl selected from pyridyl, quinolyl, imidazolyl, pyrazinyl, pyrrolyl, thienyl, thiazolyl, thiadiazolyl, pyrazolyl, triazolyl, oxazolyl and pyrimidinyl;

$R_2-R_5$ are each members selected from the group consisting of hydrogen, halo, cyano, COOR', CONR'R", CH$_2$NR'R", OR'", loweralkyl, phenyl, substituted phenyl wherein the substituent is 1-3 groups selected from loweralkyl, loweralkoxy, halo and amino, phenyl loweralkyl, and substituted phenyl loweralkyl wherein the substituent is 1-3 groups selected from loweralkyl, loweralkoxy, halo and amino, said R' and R" each being a member selected from the group consisting of hydrogen and loweralkyl and said R''' being a member selected from the group consisting of hydrogen, loweralkyl, phenyl, and substituted phenyl wherein the substituent is 1–3 groups selected from loweralkyl, loweralkoxy, halo and amino;

$R_6$ is a member selected from the group consisting of loweralkyl, phenyl and substituted phenyl wherein the substituent is 1–3 groups selected from loweralkyl, loweralkoxy, halo and amino;

$R'_7$ and $R'_8$ are each members selected from the group consisting of hydrogen, halo, loweralkyl, loweralkoxy, amino, and nitro; and $R_7$ and $R_8$ are each members selected from the group consisting of hydrogen, halo, loweralkyl, loweralkoxy, and amino.

* * * * *

UNITED STATES PATENT AND TRADEMARK OFFICE
CERTIFICATE OF CORRECTION

PATENT NO. : 4,057,547
DATED : November 8, 1977
INVENTOR(S) : Seymour Levine et al It is certified that error appears in the above-identified patent and that said Letters Patent are hereby corrected as shown below:

In Column 2, line 49, "of" should read --- by ---.

In Column 4, line 61, "ethanol" should read --- ethano ---.

In Column 6, line 27, "ethanol" should read --- ethano ---.

In Column 8, line 2, Example Vll, under $R_7$, "3-Cl" should read --- 8-Cl ---.

In Column 9, line 7, Example Vlll, under $R_4$, "-$CONH_3$" should read --- -$CONH_2$ ---.

In Column 13, line 58, "ethanol" should read --- ethano ---.

In Column 14, line 11, "ethanol" should read --- ethano ---.

Signed and Sealed this

Eighteenth Day of July 1978

[SEAL]

Attest:

RUTH C. MASON
Attesting Officer

DONALD W. BANNER
Commissioner of Patents and Trademarks